(12) United States Patent
Reinke

(10) Patent No.: US 9,829,302 B2
(45) Date of Patent: Nov. 28, 2017

(54) SYSTEM AND METHOD FOR MEASURING A NON-BONE TENDON

(71) Applicant: ALLOSOURCE, Centennial, CO (US)

(72) Inventor: Tyler A. Reinke, Littleton, CO (US)

(73) Assignee: Allosource, Centennial, CO (US)

(*) Notice: Subject to any disclaimer, the term of this patent is extended or adjusted under 35 U.S.C. 154(b) by 160 days.

(21) Appl. No.: 14/940,549

(22) Filed: Nov. 13, 2015

(65) Prior Publication Data

US 2016/0143695 A1     May 26, 2016

Related U.S. Application Data

(60) Provisional application No. 62/079,384, filed on Nov. 13, 2014.

(51) Int. Cl.
| | |
|---|---|
| *A61B 5/107* | (2006.01) |
| *G01B 5/08* | (2006.01) |
| *A61B 19/00* | (2006.01) |
| *A61B 5/00* | (2006.01) |

(52) U.S. Cl.
CPC .............. *G01B 5/08* (2013.01); *A61B 5/107* (2013.01); *A61B 5/4523* (2013.01); *A61B 19/46* (2013.01); *A61B 2019/461* (2013.01)

(58) Field of Classification Search
CPC .................................. G01B 5/08; A61B 5/107
USPC .............................. 33/511, 512, 514.1, 555.4
See application file for complete search history.

(56) References Cited

U.S. PATENT DOCUMENTS

| | | | |
|---|---|---|---|
| 3,918,166 A | 11/1975 | Mason | |
| 4,569,139 A | 2/1986 | Wakeling | |
| 4,922,622 A * | 5/1990 | Galloway | G01B 3/02 33/542 |
| 5,269,069 A | 12/1993 | Min | |
| 5,493,788 A * | 2/1996 | Richardson | A61B 5/103 33/512 |
| 5,613,302 A * | 3/1997 | Berman | G01B 5/025 33/514.2 |
| 6,904,941 B2 * | 6/2005 | Howard | F16J 10/04 138/128 |
| 2004/0107592 A1 * | 6/2004 | Matlis | A61B 5/1071 33/512 |
| 2014/0059873 A1 * | 3/2014 | Brookover | G01B 3/20 33/512 |
| 2015/0369579 A1 * | 12/2015 | Mathis | G01B 3/1082 33/701 |

* cited by examiner

*Primary Examiner* — G. Bradley Bennett
(74) *Attorney, Agent, or Firm* — James A. Sheridan; Sheridan Law, LLC

(57) ABSTRACT

There is disclosed a system and method for measuring the diameter or thickness of a tendon. In an embodiment, the device includes an adjustable tube having a variably sized cross-sectional diameter in a direction perpendicular to an axis extending between the first end and the second end, the adjustable tube being positionable from an open configuration in which the variably sized cross-sectional diameter is larger than a diameter of a tendon so as to allow loading of the tendon, to a closed configuration in which the variably sized cross-sectional diameter approximates the diameter of the tendon so as to allow measurement of the tendon. The device includes a measurement gradient in operable configuration with the adjustable tube so as to allow measurement of the tendon in the closed configuration. Other embodiments are also disclosed.

20 Claims, 6 Drawing Sheets

SYSTEM AND METHOD FOR MEASURING A NON-BONE TENDON

REFERENCE TO PENDING PRIOR PATENT APPLICATION

This application claims the benefit under 35 U.S.C. 119(e) of U.S. Provisional Patent Application No. 62/079,384, filed Nov. 13, 2014 by Tyler A. Reinke for "TENDON MEASUREMENT DEVICE," which patent application is hereby incorporated herein by reference.

BACKGROUND

An allograft includes bone, tendon, or other types of tissue that is transplanted from one person to another. Allografts are used in a variety of medical treatments, such as knee replacements, bone grafts, spinal fusions, eye surgery, and skin grafts for the severely burned. Allografts come from voluntarily donated human tissue obtained from donor-derived, living-related, or living-unrelated donors and can help patients regain mobility, restore function, enjoy a better quality of life, and even save lives in the case of cardiovascular tissue or skin.

Allograft processing centers are generally responsible for processing and cataloging allografts collected by organ procurement organizations ("OPOs"). The OPOs are, in turn, responsible for collecting and/or recovering voluntarily donated tissues and gathering any pertinent medical information about those tissues before transferring them to the processing center.

Once an allograft is received, the allograft processing center is then responsible for processing the allograft and readying it for safe and effective medical use. Such processing may involve several steps including inspection, testing, cleansing, and cataloging, all subject to strict standards and regulations.

When allografts involve tendon tissue, processing centers are often called upon by surgeons performing the tissue transplants to provide allografts with measured and identified (i.e., labeled) diameters. Specifically, when a surgeon transplants tendon tissue, it is helpful for the surgeon to know the diameter of the tendon being transplanted in order to customize a proper fit for the patient. In many cases, a surgeon may require a specific diameter for a specific patient, application, or area of the body.

Generally, the standard for measuring non-bone tendons is by means of threading or forcing the tissue through a standard "sizing block," which provides a fixed template having a number of graduated tubes in varying diameters. An exemplary sizing block of the type that exists in the prior art is shown in FIG. 1. To use a sizing block, a technician forces tendon tissue through the graduated tube that most closely approximates the diameter of the tendon to be measured and then associates the diameter of the selected tube with the diameter of the tendon. Other existing measurement devices require numerous discrete measurements along the length of an article to measured, using a cinching device that must be clamped or torqued by the user.

These existing approaches exhibit several inherent deficiencies. First, they rely on an individual user's strength and subjective judgement regarding how much force to apply during measurement. In the case of a sizing block, larger applied forces can allow a tendon to fit through a smaller measurement tube that might be unobtainable with a lesser force. Other discrete clamping or torqueing-type measurement devices rely on the user to clamp the device around the article to be measured, subjecting the measurement to variances in how hard the user can or will press.

Measurements are also skewed by the tendon's natural moisture content. Tendons exhibit semi-solid, rather than solid, properties, and moisture content differs from tendon to tendon. Differing moisture contents alter the natural lubrication of the measurement device, allowing for smoother or rougher movement of the tendon through the sizing block or other device. Tendons with higher moisture contents liberally lubricate the measurement device and slide more easily through smaller holes, while tendons with lower moisture contents experience more friction and may be perceived as larger in diameter because they resist movement.

Because existing measurement devices do not extend along the full length or even a substantial portion of a tendon, they require several discrete measurements over the length of the tendon, as well as follow-up calculations to obtain an average thickness or diameter. This "multiple measurement" method introduces additional time, steps, and variables into the process and produces a less accurate result. Also, by measuring a tendon's length at different points using a discrete ring or tube, the tendon is allowed to bulge at the edges of the device. Material that should be accounted for in the measurement is forced outward, skewing the end result.

SUMMARY

This Summary is provided to introduce a selection of concepts in a simplified form that are further described below in the Detailed Description. This Summary is not intended to identify key aspects or essential aspects of the claimed subject matter. Moreover, this Summary is not intended for use as an aid in determining the scope of the claimed subject matter One embodiment provides a tendon measurement device. The tendon measurement device includes an adjustable tube having a first end, a second end, and a variably sized cross-sectional diameter in a direction perpendicular to an axis extending between the first end and the second end, where the adjustable tube is positionable between an open configuration in which the variably sized cross-sectional diameter is larger than a diameter of a tendon so as to allow loading of the tendon and a closed configuration in which the variably sized cross-sectional diameter approximates the diameter of the tendon so as to allow measurement of the tendon. The tendon measurement device also includes a measurement gradient operably associated with the adjustable tube so as to allow measurement of the tendon when the adjustable tube is positioned in the closed configuration.

Another embodiment provides a system for measuring a diameter of a length of tendon. The system includes a cinchable tube configured to move between an open position and a closed position. When in the open position, the cinchable tube is configured to receive at least half the length of the tendon and when in the closed position, said cinchable tube is configured to close about the at least half the length of the tendon such that the cinchable tube approximates the diameter of the tendon. The system also includes a measurement gradient configured to display the diameter of the tendon when the cinchable tube is in the closed position.

Yet another embodiment provides a method for measuring a diameter of a non-bone tendon using a tendon measurement device having an adjustable tube positionable between an open configuration and a closed configuration and a measurement gradient associated with the adjustable tube. The method includes (1) when the adjustable tube is positioned in the open configuration, inserting the tendon into the adjustable tube such that no force is applied to the tendon; (2) activating the adjustable tube to move the adjustable tube from the open configuration to the closed configuration such that a calibrated maximum force is applied to the tendon; and (3) when the adjustable tube is positioned in the closed configuration, identifying the diameter of the tendon as reflected on the measurement gradient.

Other embodiments are also disclosed.

Additional objects, advantages and novel features of the technology will be set forth in part in the description which follows, and in part will become more apparent to those skilled in the art upon examination of the following, or may be learned from practice of the technology.

BRIEF DESCRIPTION OF THE DRAWINGS

Non-limiting and non-exhaustive embodiments of the present invention, including the preferred embodiment, are described with reference to the following figures, wherein like reference numerals refer to like parts throughout the various views unless otherwise specified. Illustrative embodiments of the invention are illustrated in the drawings, in which.

DETAILED DESCRIPTION

Embodiments are described more fully below in sufficient detail to enable those skilled in the art to practice the system and method. However, embodiments may be implemented in many different forms and should not be construed as being limited to the embodiments set forth herein. The following detailed description is, therefore, not to be taken in a limiting sense.

Various embodiments of the systems and methods described herein relate to the measurement of a diameter or thickness of a cylindrical shaped object such as, for example, a non-bone allograft tendon used in the medical industry, as discussed in the Background section above. More specifically, embodiments include a tendon measurement device with components configured to cinch or close about a tendon using a ratcheting mechanism designed to apply torque until a calibrated maximum force is applied to the tendon. In this regard, a cylinder or tube of the tendon measurement device may be configured to close around an at-rest tendon and, after reaching its torqueing limit in various embodiments, provide an indication of the diameter of the tendon disposed therein.

Figure 1:
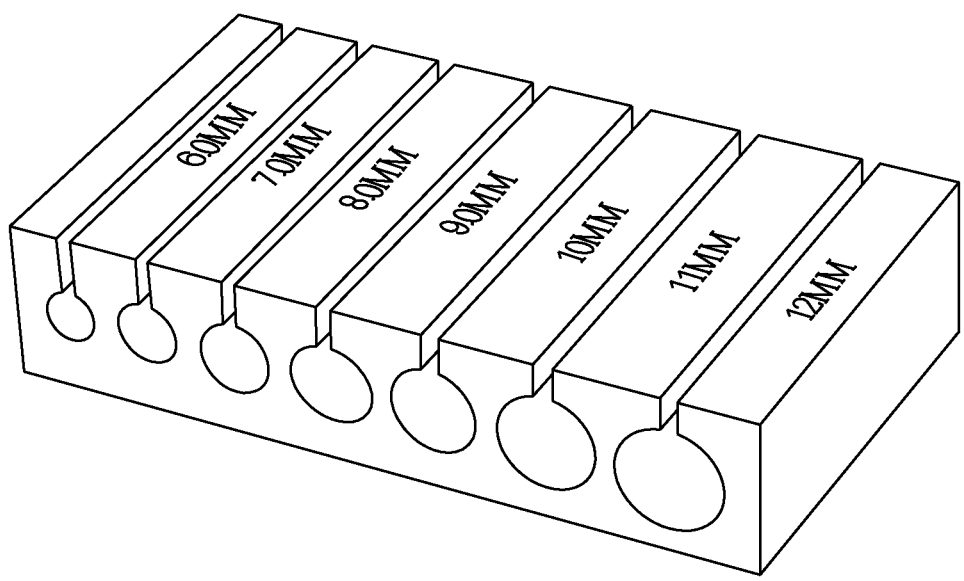
FIG. 1 illustrates a perspective view of a prior art sizing block currently used to measure the diameter of non-bone tendons.
Figure 2:
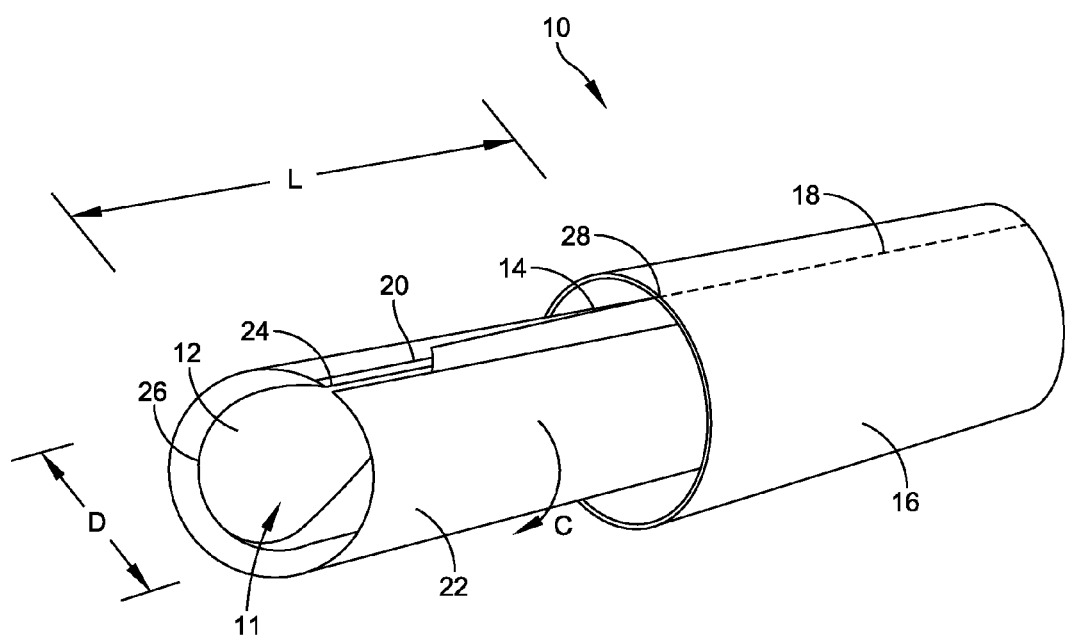
FIG. 2 illustrates a perspective exploded view of one embodiment of a tendon measurement device in an open configuration for loading a tendon to be measured.

FIG. 2 provides an exploded perspective view of one embodiment of a tendon measurement device 10 in an open configuration 11. In this embodiment, tendon measurement device 10 may include an adjustable or cinching tube 12 that is adjustably positionable with respect to an outer tube 16. In further detail, adjustable tube 12 may have a first edge 14 that affixes to outer tube 16, either continuously or at one or more points along a first connection seam 18. Adjustable tube 12 may also include a second edge 20 that affixes to a ratcheting mechanism such as, in this embodiment, a rotatable tube 22 disposed between outer tube 16 and adjustable tube 12 when adjustable tube 12 is in open configuration 11. This connection may occur continuously or at one or more points along a second connection seam 24. Connections seams 18 and 24 may extend as lines, as shown, or be joined at or adjacent to the illustrated lines in any appropriate and/or desired configuration and with any appropriate fasteners and/or adhesives. When in open configuration 11, adjustable tube 12 may have an open diameter, D, that exceeds a diameter of the tendon, or that is large enough to receive the tendon without placing pressure or force on the tendon to be measured.

Figure 3:
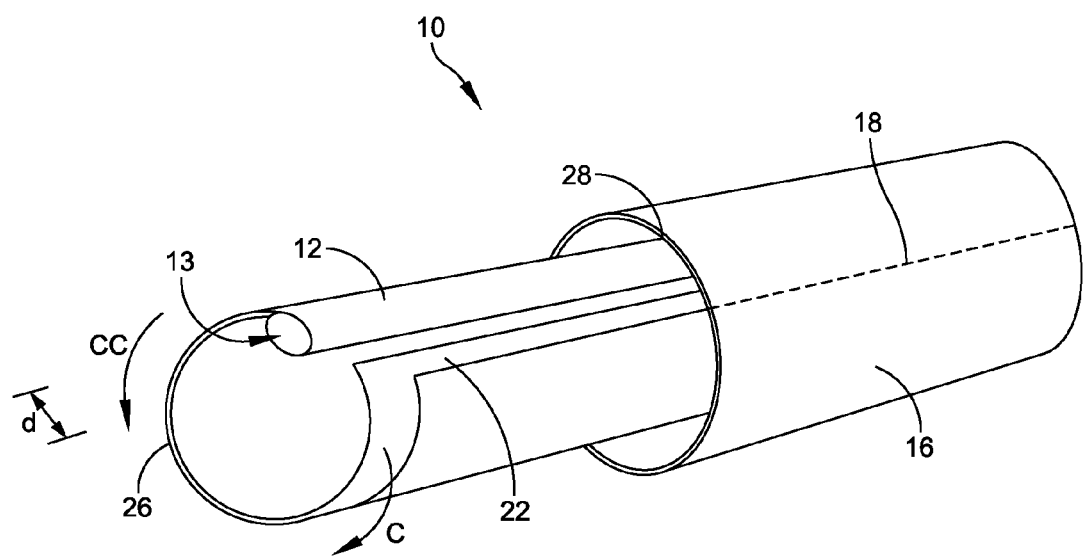
FIG. 3 illustrates the tendon measurement device of FIG. 2 in a closed configuration to closely approximate the tendon so as to allow alignment of measurement indicia to provide a measurement of the diameter of the tendon.

FIG. 3 illustrates an exploded perspective view of tendon measurement device 10 in a closed configuration 13. To move between open configuration 11 (FIG. 2) and closed configuration 13 (FIG. 3), rotatable tube 22 may be rotated such that second edge 20/connection seam 24 (FIG. 2) rotates toward first edge 14/connection seam 18 of adjustable tube 12 and outer tube 16. This rotation causes rotatable tube 22 to curl into adjustable tube 12 along connection seam 24 (FIG. 2) and leverage that movement against fixed connection seam 18 with outer tube 16, thereby cinching or closing rotatable tube 12 about the tendon to be measured. In this embodiment, the motion of rotatable tube 22 proceeds in a clockwise direction, denoted by arrow C, relative to outer tube 16. Ultimately, the cinching motion results in a smaller diameter, d, of closed configuration 13 (FIG. 3), which closely approximates a diameter of the tendon under measurement.

To return to open configuration 11 from closed configuration 13, the direction of rotation of rotatable tube 22 may be reversed such that, in one embodiment, rotatable tube 22 is turned in a counterclockwise direction, denoted by arrow CC in FIG. 3. While the rotational directions of rotatable tube 22 are described as moving clockwise from open configuration 11 to closed configuration 13 and counter-clockwise from closed configuration 13 to open configuration 11, it will be understood that tendon measurement device 10 could be engineered such that the opposite is true. Further, while in this embodiment the ratcheting mechanism is provided by rotatable tube 22, the ratcheting mechanism that adjusts or actuates adjustable tube 12 between open and closed configurations 11, 13 may be a component of any appropriate size, shape, and/or configuration.

To ensure consistent force or pressure is applied to each tendon under measurement, regardless of user strength or preference, rotatable tube 22 may be configured to rotate, or apply torque, until a calibrated maximum force is achieved between adjustable tube 12 and the tendon being measured as measurement device 10 moves between open and closed configurations 11 and 13, respectively. This approach results in a consistent diameter or thickness measurement for each tendon. To achieve a consistent calibrated maximum force, rotatable tube 22 may be rotated manually or electromechanically. In the case of an embodiment employing manual rotation of rotatable tube 22, a commercially available torque brake or joint (not shown) may be installed relative to rotatable tube 22 and outer tube 16, such that the brake trips or catches once the calibrated maximum force is achieved. As a result, the user either cannot rotate tube 22 beyond the calibrated maximum force or is notified as the maximum is reached. Other embodiments of tendon measurement device 10 may employ a servo motor or stepper motor (not shown) to rotate rotatable tube 22. In these embodiments, the motor's controller may be programmed with position or force-limiting controls, either working in conjunction with a torque-sensor feedback loop or by limiting current in a manner that controls the maximum force applied to the tendon. This approach allows the motor to rotate rotatable tube 22, and therefore cinch adjustable tube 12, until the predetermined calibrated maximum force is achieved against the tendon in closed configuration 13. After achieving the calibrated maximum force, the motor may hold the force constant for a period of time (i.e., to allow the user to log a measurement) before later reversing to open configuration 11.

Adjustable tube 12 may also include a first end 26 and a second end 28, with a length, L, spanning the distance there between. In one embodiment, length, L, may equal or exceed at least half a length of the tendon under measurement. In other embodiments, length, L, may approximate the length of the tendon or exceed the length of the tendon. This longer cylinder or tube-like measurement system allows the diameter of the tendon to be measured in one continuous measurement, as opposed to requiring numerous discrete measurements that must then be tallied and/or averaged. In addition, ensuring that the whole or substantially the whole of the tendon is consistently compressed for measurement, rather than only a discrete cross-sectional portion, prevents the tendon from bulging or reshaping beyond the sides of measurement device 10. This results in a more accurate diameter measurement of the tendon.

Figure 4:
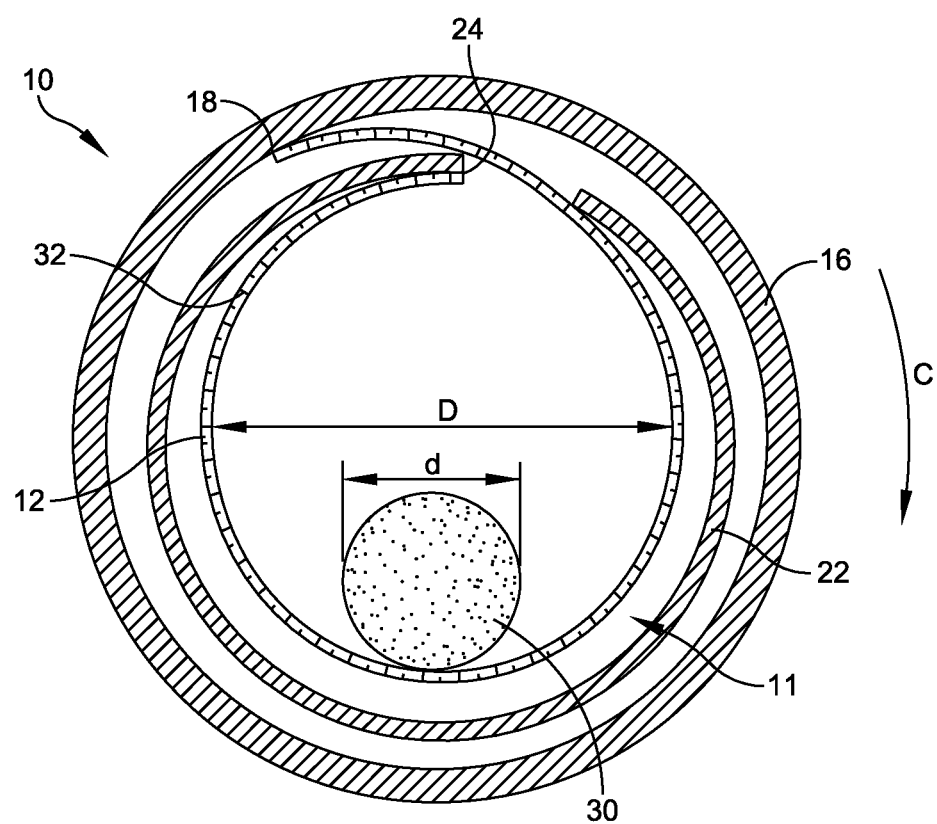
FIG. 4 illustrates a front view of the tendon measurement device of FIGS. 2-3 with a tendon loaded within an adjustable tube positioned in an open configuration.

Non-bone tendons exhibit unique semi-solid properties in that, while technically solid, they are malleable and contain varying moisture levels. Forceful manipulation of the tendon while installing the tendon upon a measurement device such as a sizing block, discussed above, may impact the ultimate diameter or thickness measurement due to reshaping and uneven compression of the tendon during loading. In addition, a tendon with a high moisture content may lubricate the sides of a measurement device if forcefully squeezed into place, and varying lubrication of a measurement device can change the measurement result. Tendon measurement device 10 provides an elegant solution to these challenges. FIG. 4 illustrates a front view of tendon measurement device 10 in open configuration 11 and supporting a loaded tendon 30 to be measured. Notably, tendon 30 may be loaded within adjustable tube 12 without the need to forcefully string, push, or pull tendon 30 into position because the variable diameter, D, of adjustable tube 12 exceeds the diameter, d, of tendon 30 when adjustable tube 12 is in open configuration 11. As a result, tendon 30 is received within adjustable tube 12 in its natural, at-rest state, creating an unbiased measurement platform.

Figure 5:
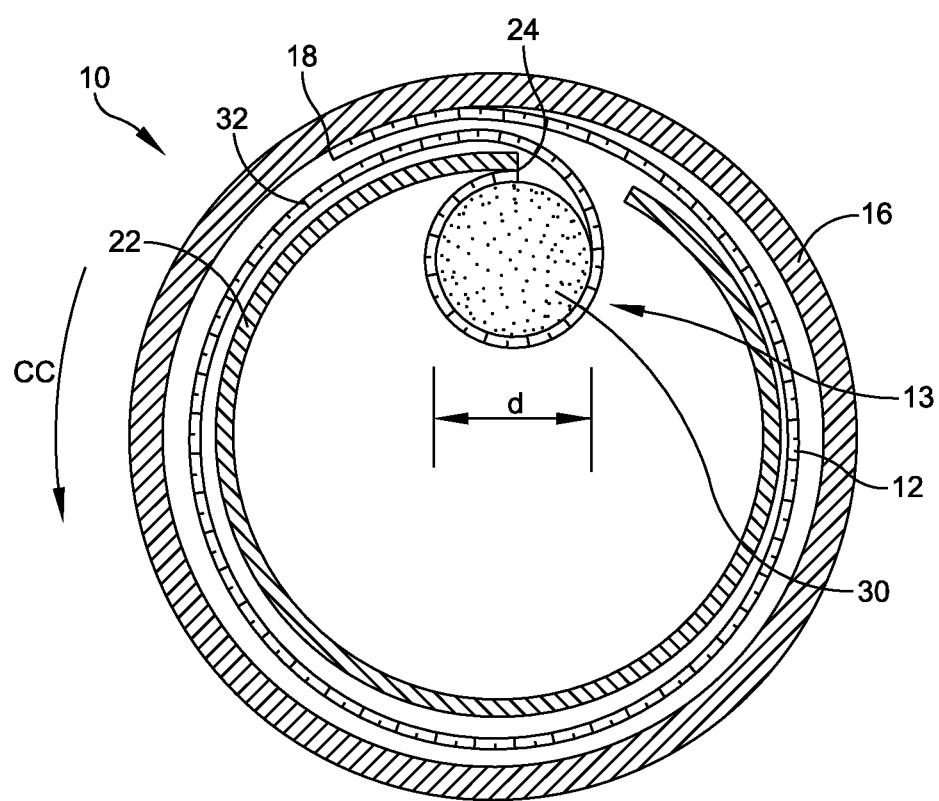
FIG. 5 illustrates a front view of the tendon measurement device of FIG. 4 with the adjustable tube actuated to a closed configuration to closely approximate the tendon so as to allow alignment of measurement indicia to provide a measurement of the diameter of the tendon.

FIG. 5 illustrates a front view of tendon measurement device 10 in closed configuration 13 for taking a diameter measurement of tendon 30. To achieve this measurement, a measurement gradient may be associated with measurement device 10 to facilitate the identification and recording of diameter, d, of tendon 30. In one exemplary embodiment, the measurement gradient may take the form of a series of measurement indicia 32 (i.e., a ruler) associated with adjustable tube 12. Measurement indicia 32 may be configured such that a reading taken at connection seam 24 provides a measurement of the diameter, d, of tendon 30 via reference of the position of adjustable tube 12 with respect to seam 24. While this placement/configuration of measurement indicia 32 provides one alternative, it should be noted that measurement indicia 32 may be located at and/or configured in any appropriate manner that results in the most accurate and convenient diameter measurement.

In another embodiment, the measurement gradient may take the form of a digital display (not shown) output from an electromechanical torqueing device such as a servo or stepper motor tasked with rotating rotatable tube 22. That is, the motor may be programmed to calculate diameter, d, of tendon 30 as a function of the number of rotations of rotatable tube 22 that are executed (i.e., a displacement of adjustable tube 12) before arriving at the calibrated maximum force.

Embodiments of tendon measurement device 10 may be used within laboratory and surgical settings to measure the diameter of non-bone tendons. This data may be used to size tendons in a uniform manner, independent of the varying strengths and techniques of individual users and without requiring numerous discrete measurements and follow-up calculations, all of which introduce error into the measurement process. By subjecting the tendon under measurement to a uniform calibrated maximum force along the whole or substantially the whole of the tendon, and by removing the need for the tendon to be forced through a pre-sized measurement hole, a user may obtain a reliable, consistent measurement along the full length of the equally compressed tendon, free of the inherent deficiencies of existing measurement devices.

Using tendon measurement device 10, a lab technician packaging a tendon and a surgeon are equally able to use the device and record the same results from the same tendon, whereas currently there is not a "standard" device to take measurements without variables in dimensions arising from pulling force, unequal pressure applied at discrete measurement points, or tendon moisture content and varying device lubrication. Measurement device 10 provides a solution not only for allograft processing centers, but also to surgeons for use during surgery over their pre-existing tendon measuring devices, or to any entity that requires accurate tendon or soft tissue (tendon-like) measurements, including hospitals, Organ Procurement Organizations, and other tissue and bone graft manufacturers.

Components of tendon measuring device 10 may be manufactured with a heat resistant plastic or metal so as to ensure that the device could be sterilized within an autoclave.

Figure 6:
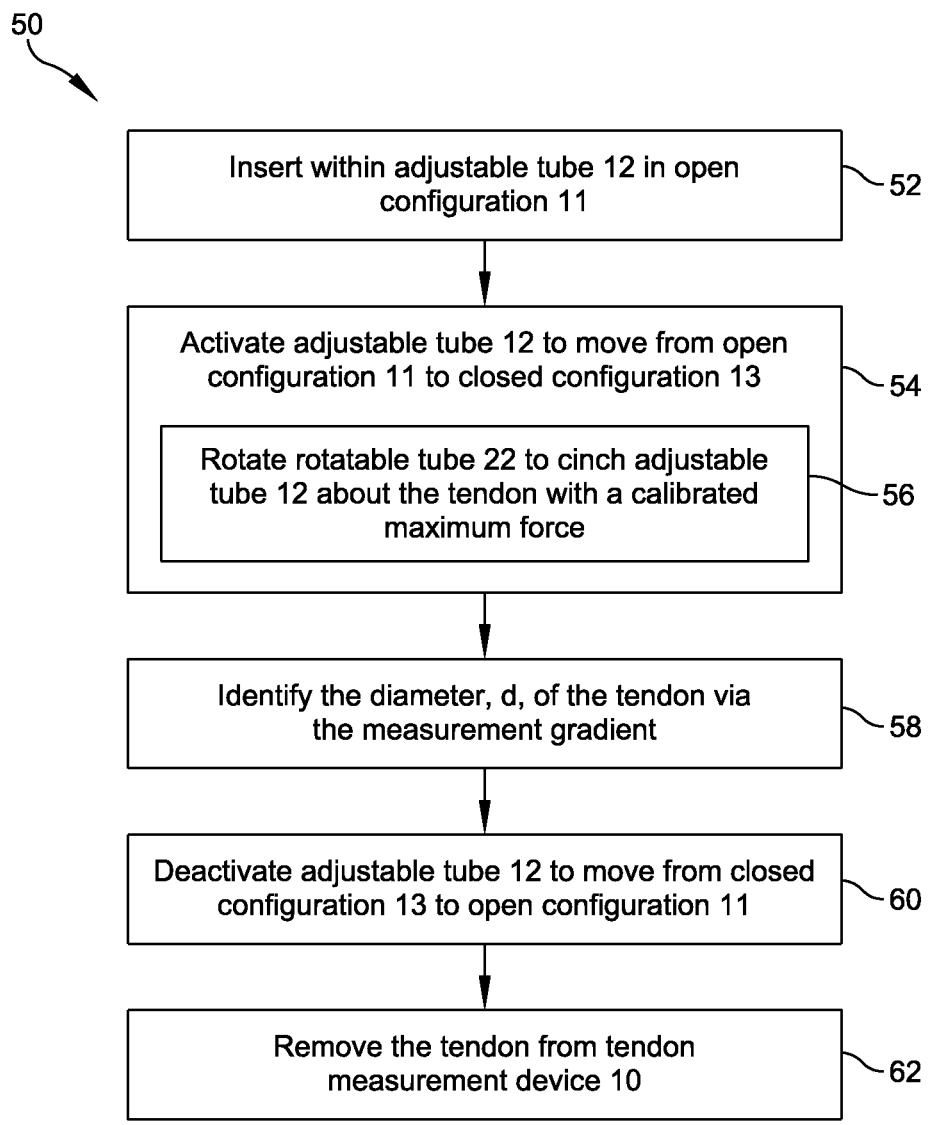
FIG. 6 provides a flow chart depicting an exemplary method for measuring the diameter of a tendon using the tendon measurement device of FIGS. 2-5.

FIG. 6 provides a flow chart detailing an exemplary method 50 for measuring a diameter of a tendon. Method 50 begins when a length of tendon (e.g., a length exceeding half the length of the tendon, a substantial whole of the tendon) is loaded or inserted (52) within adjustable tube 12 of measurement device 10, where adjustable tube 12 is in open configuration 11. Because an inner diameter, D, of adjustable tube 12 is larger than the diameter, d, of the tendon when adjustable tube is in open configuration 11, inserting (52) the tendon doesn't apply force or pressure to the tendon. Method 52 continues with the activation (54) of adjustable tube 12 to move adjustable tube 12 from open configuration 11 (FIGS. 2 and 4) to closed configuration (FIGS. 3 and 5) in which the length of the tendon is put under a uniform calibrated maximum force. In one embodiment, this activation (54) may include rotating (56) rotatable tube 22 in a clockwise direction, C, to move second edge 20 of adjustable tube 12 inward toward first edge 14 of adjustable tube 12, such that adjustable tube 12 curls or cinches about the tendon until the calibrated maximum force is achieved. Once in closed configuration 13, the user may identify (58) the diameter, d, of the tendon by taking a reading from the measurement gradient, which may, in one embodiment, take the form of measurement indicia 32 associated with adjustable tube 12 or any other appropriate component of measurement device 10. In another embodiment, the measurement gradient may take the form of a digital readout on a display, as calculated as a function of the number of rotations of rotatable tube 22 in achieving the calibrated maximum force. Once the diameter, d, has been identified (58), adjustable tube 12 may be deactivated (60) to move from closed configuration 13 to open configuration 11, such that the tendon may be removed (62) from measurement device 10.

Although the above embodiments have been described in language that is specific to certain structures, elements, compositions, and methodological steps, it is to be understood that the technology defined in the appended claims is not necessarily limited to the specific structures, elements, compositions and/or steps described. Rather, the specific aspects and steps are described as forms of implementing the claimed technology. Since many embodiments of the technology can be practiced without departing from the spirit and scope of the invention, the invention resides in the claims hereinafter appended.

What is claimed is:

1. A tendon measurement device, comprising:
an adjustable tube having a first end, a second end, and an inner region having a variably sized cross-sectional diameter in a direction perpendicular to an axis extending between said first end and said second end, said adjustable tube positionable between an open configuration in which said inner region of said variably sized cross-sectional diameter is larger than a diameter of a tendon so as to allow loading of the tendon within the inner region and a closed configuration in which said inner region of said variably sized cross-sectional diameter approximates the diameter of the tendon within said inner region so as to allow measurement of the tendon within said inner region; and
a measurement gradient operably associated with said adjustable tube so as to allow measurement of the tendon within said inner region when said adjustable tube is positioned in said closed configuration.

2. The device of claim 1, further comprising an outer tube encompassing said adjustable tube, said outer tube affixed to a first edge of said adjustable tube, and said adjustable tube adjustably positionable with respect to said outer tube.

3. The device of claim 2, wherein said measurement gradient provides an indication of the diameter of the tendon.

4. The device of claim 2, further comprising a ratcheting mechanism operably configured to position said adjustable tube between said open configuration and said closed configuration.

5. The device of claim 4, wherein said ratcheting mechanism comprises a rotatable tube, said rotatable tube affixed to a second edge of said adjustable tube and positioned between said adjustable tube and said outer tube when said adjustable tube is in said open configuration.

6. The device of claim 1, wherein said adjustable tube has a length from said first end to said second end, and wherein said length of said adjustable tube exceeds a length of the tendon under measurement.

7. The device of claim 1, wherein said adjustable tube has a length from said first end to said second end, and wherein said length of said adjustable tube approximates a length of the tendon under measurement.

8. The device of claim 1, wherein said adjustable tube has a length from said first end to said second end, and wherein said length of said adjustable tube equals a length of the tendon under measurement.

9. The device of claim 1, wherein said adjustable tube has a length from said first end to said second end, and wherein said length of said adjustable tube is at least half a length of the tendon under measurement.

10. A system for measuring a diameter of a length of tendon, comprising:
a cinchable tube defining an inner region, said cinchable tube configured to move between an open position and a closed position, wherein when in said open position, said cinchable tube is configured to receive at least half the length of the tendon within said inner region and when in said closed position, said cinchable tube is configured to close about the at least half the length of the tendon within said inner region such that said cinchable tube approximates the diameter of the tendon; and
a measurement gradient configured to display the diameter of the tendon within said inner region when said cinchable tube is in said closed position.

11. The system of claim 10, wherein said cinchable tube has a length that exceeds at least half the length of the tendon under measurement.

12. The system of claim 10, wherein said measurement gradient comprises a number of measurement indicia associated with a diameter within said inner region of said cinchable tube.

13. The system of claim 10, wherein said system further comprises:
an outer tube, said outer tube enveloping said cinchable tube and attached to a first edge of said cinchable tube; and
a ratcheting mechanism, said ratcheting mechanism affixed to a second end of said cinchable tube and adapted to rotate in a manner that leverages said cinchable tube against said outer tube and causes said cinchable tube to move from said open position to said closed position.

14. The system of claim 10, wherein when in said open position, said cinchable tube does not apply force to the tendon.

15. The system of claim 14, wherein when in said closed position, said cinchable tube wraps about the tendon with a calibrated maximum force.

16. A method for measuring a diameter of a non-bone tendon using a tendon measurement device including an adjustable tube positionable between an open configuration and a closed configuration and a measurement gradient associated with a diameter within an inner region of said adjustable tube, comprising:
when said adjustable tube is positioned in said open configuration, inserting the tendon into said inner region said adjustable tube such that no force is applied to the tendon;
activating said adjustable tube to move said adjustable tube from said open configuration to said closed configuration such that a calibrated maximum force is applied to the tendon within said inner region; and when said adjustable tube is positioned in said closed configuration, identifying the diameter of the tendon within said inner region as reflected on said measurement gradient.

17. The method of claim 16, wherein said tendon measurement device further comprises an outer tube attached to a first edge of said adjustable tube and a ratcheting mechanism affixed to a second edge said adjustable tube, and wherein said activating said adjustable tube comprises rotating said ratcheting mechanism such that said second edge rotates toward said first edge, thereby causing said adjustable tube to cinch from said open configuration to said closed configuration.

18. The method of claim 17, wherein said ratcheting mechanism comprises a rotatable tube disposed between said adjustable tube and said outer tube when said adjustable tube is in said open configuration.

19. The method of claim 18, wherein said rotating said ratcheting mechanism comprises turning said rotatable tube by hand.

20. The method of claim 16, where said adjustable tube has a length that at least exceeds half a length of the tendon.

* * * * *